United States Patent [19]

Pews

[11] Patent Number: 4,486,590

[45] Date of Patent: Dec. 4, 1984

[54] PREPARATION OF 2-T-BUTYL-5-CHLOROPYRIMIDINE

[75] Inventor: Richard G. Pews, Midland, Mich.

[73] Assignee: The Dow Chemical Company, Midland, Mich.

[21] Appl. No.: 404,268

[22] Filed: Aug. 2, 1982

[51] Int. Cl.$^3$ .......................................... C07D 239/30
[52] U.S. Cl. .................. 544/334; 544/243; 544/321; 544/323
[58] Field of Search .......................................... 544/334

[56] References Cited

U.S. PATENT DOCUMENTS 2,812,328  11/1957  Hepworth .......................... 544/334
4,299,961  11/1981  Pasquale et al. ................... 544/334

OTHER PUBLICATIONS

Blank, "Chemical Abstracts", vol. 89, 1978, col. 90167z.

*Primary Examiner*—Glennon H. Hollrah
*Assistant Examiner*—James H. Turnipseed

[57] ABSTRACT

2-t-Butyl-5-chloropyrimidine is made by the direct chlorination of 2-t-butylpyrimidine with elemental chlorine in an acetic or propionic acid solution at temperatures of 40° to 90° C. in the presence of a buffer.

5 Claims, No Drawings

PREPARATION OF 2-T-BUTYL-5-CHLOROPYRIMIDINE

BACKGROUND OF THE INVENTION

In "Heterocyclic Compounds, The Pyrimidines, Supplement 1" (1970) Wiley-Interscience, page 119, it is stated that "Chlorination using elemental chlorine is seldom easy in practice and yields are rather indifferent." However, pyrimidines having amino, hydroxy or methoxy activating groups have been chlorinated under carefully controlled conditions, e.g. 2,4-diamino-6-chloropyrimidine and 4,6-dihydroxy-2-phenylpyrimidine. In "Heterocyclic Compounds, The Pyrimidines" (1962) Wiley-Interscience, page 8, it is taught that the introduction of election-releasing substituents into any position of the pyrimidine ring makes the 5-position readily halogenatable.

SUMMARY OF THE INVENTION

I have now found that 2-t-butyl-5-chloropyrimidine may be made in good yields and purity by the direct chlorination of 2-t-butylpyrimidine with elemental chlorine in an acetic or propionic acid solution at temperatures of 40° to 90° C., and preferably in the presence of a buffer.

This compound is described and claimed in copending application Ser. No. 389,638 filed June 18, 1982 and is advantageously employed as an intermediate in the preparation of O-alkyl-O-[pyrimidin(5)yl]-(thiono)(thiol)-phosphoric (phosphonic) acid esters or ester amides having exceptional insecticidal activity by the processes described in U.S. Pat. No. 4,127,652 or copending application Ser. No. 928,665 filed July 28, 1978 now U.S. Pat. No. 4,429,125, issued Jan. 31, 1984. For such processes, the halopyrimidines are first hydrolyzed as taught in Supplement I of "The Pyrimidines", Interscience (1970), page 148 or in copending application Ser. No. 301,686, filed Sept. 14, 1981 now U.S. Pat. No. 4,379,930 issued Apr. 12, 1983.

DETAILED DESCRIPTION OF THE INVENTION

The reaction is preferably carried out at temperatures of 55° to 65° C. and in the absence of a catalyst. The solution of 2-t-butylpyrimidine preferably contains from 1.5 to 3.0 moles pyrimidine per liter of solvent, although higher or lower amounts may be employed if desired. In more dilute solutions, greater energy requirements must be met in order to separate the desired product and chlorination of the solvent itself is more apt to take place. In more concentrated solutions, it is more difficult to maintain a uniform mixture or solution because of increased viscosity.

Suitable buffers include, for example, sodium acetate, potassium acetate, sodium propionate and potassium propionate. It is desirable that the buffer be soluble in the solvent. Sodium acetate is preferred.

The preferred solvent is acetic acid.

The invention is further illustrated by the following examples where all parts are by weight unless otherwise specified.

| Run | t-Butylpyrimidine (moles) | Acetic Acid (ml) | Sodium Acetate (Moles) | Temperature (°C.) | Time, hrs | Yield |
|-----|---------------------------|------------------|------------------------|-------------------|-----------|-------|
| 1 | 0.022 | 25 | 0.026 | 60 | 4.5 | 97 |
| 2 | 0.367 | 250 | 0.44 | 60 | 6.0 | 75 |
| 3 | 0.734 | 500 | 0.88 | 60 | 6.0 | 86 |
| 4 | 0.734 | 500 | 0.88 | 60 | 6.0 | 97 |
| 5 | 0.734 | 500 | 0.88 | 60 | 6.0 | 73 |
| 6 | 0.1 | 68 | 0.12 | 60 | 3.5 | 83 |
| 7 | 1.47 | 500 | 1.76 | 60 | 13.0 | 79 |
| 8 | 1.47 | 500 | 1.76 | 60 | 10.5 | 82 |

Similar results may be obtained when employing propionic acid as the solvent and/or utilizing other buffers such as, for example, potassium acetate, sodium propionate and potassium propionate.

Various modifications may be made in the present invention without departing from the spirit or scope thereof and it is understood that I limit myself only as defined in the appended claims.

I claim:

1. Process for the preparation of 2-t-butyl-5-chloropyrimidine which comprises chlorinating 2-t-butylpyrimidine in acetic or propionic acid solution with elemental chlorine in the absence of a catalyst at temperatures of from 40° to 90° C.

2. Process of claim 1 wherein the reaction temperature is from 55° to 65° C.

3. Process of claim 2 wherein the reaction is carried out for from 3 to 15 hours.

4. Process of claim 1 wherein the solvent is buffered with sodium acetate.

5. Process of claim 4 wherein the solvent is acetic acid.

* * * * *